(12) United States Patent
Chapuis

(10) Patent No.: US 6,350,910 B1
(45) Date of Patent: *Feb. 26, 2002

(54) STEREOSPECIFIC ISOMERISATION OF ALLYLAMINES WITH THE AID OF IMMOBILIZED PHOSPHORATED CHIRAL LIGANDS

(75) Inventor: Christian Chapuis, Mies (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/588,687

(22) Filed: Jun. 7, 2000

(30) Foreign Application Priority Data

Jun. 17, 1999 (CH) .............................................. 1131/99

(51) Int. Cl.[7] .................................................. C07F 9/02
(52) U.S. Cl. ...................... 564/271; 564/276; 564/278; 564/305; 564/444; 564/509; 568/13
(58) Field of Search ................................ 564/305, 444, 564/509, 271, 276, 278; 568/13

(56) References Cited

U.S. PATENT DOCUMENTS

| | | | |
|---|---|---|---|
| 4,605,750 A | 8/1986 | Kumobayashi et al. | ......... 556/7 |
| 4,695,631 A | 9/1987 | Otsuka et al. | ............... 544/170 |
| 4,861,890 A | 8/1989 | Heiser et al. | ............... 546/184 |
| 5,488,172 A | 1/1996 | Cereghetti et al. | ............. 568/13 |
| 5,510,503 A | 4/1996 | Laue et al. | .................... 556/21 |
| 6,020,527 A | * 2/2000 | Chapuis et al. | ............. 564/248 |

FOREIGN PATENT DOCUMENTS

| | | |
|---|---|---|
| EP | 0 068 506 | 1/1983 |
| EP | 0 135 392 | 8/1985 |
| EP | 0 156 607 | 10/1985 |
| EP | 0 170 470 | 2/1986 |
| EP | 0 398 132 | 11/1990 |
| EP | 0 643 065 | 3/1995 |
| JP | 61-19203 | 8/1987 |
| WO | WO 95/21176 | 8/1995 |
| WO | WO 98/12202 | 3/1998 |

OTHER PUBLICATIONS

Inoue et al., 'Medchanism of the asymmetric isomerization of allylamines to enamines catalyzed by 2,2'–bis(diphenylphosphino)–1,1'–binaphthyl–rhodium complexes.' J. Am. Chem. Soc. 1990, 112, pp. 4897–4905, 1990.*

M. Reggelin, "Polymere Katalysatorent", *Nach. Chem. Tech. Lab.* 45 (1997) 1196–1201.

K. Takabe et al., "Telomerization of Isoprene with Dialkylamine: N,N–Diethylnerylamine", *Org. Synth.* 1998 (67), 48.

K. Tani et al., "Highly Enantioselective Isomerization of Prochiral Allylamines Catalyzed by Chiral Diphosphine Rhodium (I) Complexes. Preparation of Optically Active Enamines", *J. Am Chem. Soc.* 1984 (106) 5208–5217.

K. Tani, "Asymmetric Isomerization of Allylic Compounds and the Mechanism", *Pure & Appl. Chem.* 1985 (57) 1845–1854.

* cited by examiner

*Primary Examiner*—Sreeni Padmanabhan
*Assistant Examiner*—Brian J. Davis
(74) *Attorney, Agent, or Firm*—Winston & Strawn

(57) ABSTRACT

The present invention describes a method for stereospecific isomerisation of prochiral allylamines into enamines and chiral imines, by using catalysts of Rh, Ir and Ru having phosphine chiral ligands immobilised on a solid material. The immobilised ligands are derivatives of phosphines of the type bis(diphenylphosphino)biaryl such as, for example, the phosphine known by the name BINAP. The method is particularly suitable for the production of optically active citronellal which may be obtained in optical purities above 95%.

15 Claims, No Drawings

STEREOSPECIFIC ISOMERISATION OF ALLYLAMINES WITH THE AID OF IMMOBILIZED PHOSPHORATED CHIRAL LIGANDS

TECHNICAL FIELD

The present invention relates to the field of organic catalytic synthesis. More particularly, it concerns a method for stereospecific isomerisation of allylamines, such as those defined by formula (I) below, using complexes of certain transition metals having, as ligands, chiral phosphorated compounds immobilised by fixation on to a suitable polymer.

PRIOR ART

Isomerisation reactions of prochiral and non-prochiral allylamines, with the aid of complexes of rhodium, iridium or ruthenium have already been known for several years; examples are those represented by the formulae [Rh(P—P) *diene]$^+$X$^-$, [Rh(P—P)*$_2$]$^+$X$^-$, [Ru(CH$_3$COO)$_2$(P—P)* ] or [RuY$_2$(P—P)*], in which (P—P)* is a phosphorated, bidentate chiral ligand, "diene" represents a diolefin such as cyclo-octadiene or norbornadiene, X$^-$ is an anion such as a halide, BF$^-_4$, PF$^-_6$ or ClO$^-_4$, and Y is a halide. The isomerisation reaction gives rise to the corresponding enamines or imines, which are then hydrolysed to obtain chiral aldehydes, for example citronellal, methoxycitronellal or hydroxycitronellal. These compounds are highly valued materials in perfumery.

These known methods are the subject matter of several publications. Of these one may cite the patents EP-B-068 506, 135 392 and 156 607 (holder: Takasago Perfumery Co.) and JP 61-19203 of the same holder, as well as patent EP-B-398 132 (holder: Hoffmann La Roche AG) and patent application EP 643 065 (applicant: Bayer AG). All the methods described in these reference documents use catalysts having, as the ligand, bidentate chiral phosphines based on biphenyl or binaphthyl systems of symmetry C$_2$. The most well-known ligand for this isomerisation reaction, and which is also used in other catalytic methods, is BINAP, represented by the following formula (IV):

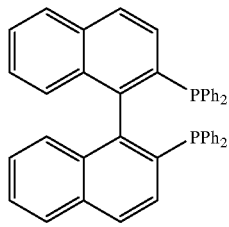

(IV)

Ph = phenyl

One drawback of the use of the catalysts mentioned above resides in the fact that it is difficult to separate the catalyst from the product obtained. The normal method used for obtaining a pure product is distillation of the reaction mixture, obtained by degrading the catalyst, which is then no longer usable.

The chemical literature proposes the fixation on to polymers of ligands known for their use in catalytic reactions, so as to solve the problems of separation of the product from the reaction mixture and of decomposition of the catalyst still present in this mixture. A general account of the existing knowledge in this field may be found in the article of M. Reggelin in Nach. Chem. Tech. Lab. 45(1997), pages 1196–1201.

Application WO 98/12202 of Oxford Asymmetry Limited describes ligands of the BINAP type such as those mentioned above, which are attached to suitable polymers such as, for example, polystyrene, polyamides or aminomethylated polystyrene, by spacer groups comprising, for example, —O—C(O)—, —NH—C(O)—, —O— or —NH— functions linked to alkyl chains. In the examples, this same application also describes the use of these ligands immobilised for the asymmetric hydrogenation of ketones and olefins.

Although the data reveal that these ligands yield roughly the same conversions and enantioselectivities as non-immobilised BINAP, nowhere can a precise indication be found of the nature of the products obtained and of the reaction conditions. Overall, the application reveals that immobilised ligands of the BINAP type, which no longer have the C$_2$ symmetry of non-immobilised BINAP, can be used in asymmetrical hydrogenations. However, and also due to the fact that not all the necessary information permitting estimation of the true catalytic capacity of these ligands is available, the person skilled in the art is not capable of deducing that ligands of the immobilised BINAP type prove equally effective in asymmetric isomerisation reactions of allylamines.

DESCRIPTION OF THE INVENTION

The aim of the present invention is to find an immobilised ligand which avoids the problems of non-immobilised ligands as stated above, and which is just as effective in respect of conversions and enantioselectivity as the latter in the asymmetric isomerisation of prochiral allylamines.

The aim is achieved by a method for stereospecific isomerisation of prochiral allyl systems represented by the formula

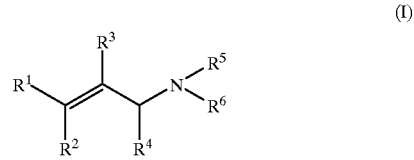

(I)

in which R$^1$≠R$^2$, and each represents an alkyl or alkenyl group, containing 1 to 12 carbon atoms, or an aryl group, possibly substituted by a hydroxy group, R$^3$ and R$^4$ representing independently of one another hydrogen, a C$_1$ to C$_{12}$ alkyl or alkenyl group, or an aryl group, R$^5$ is hydrogen or an alkyl or cycloalkyl group, containing 1 to 8 carbon atoms, R$^6$ is an alkyl or cycloalkyl group, containing 1 to 8 carbon atoms, or R$^5$ and R$^6$ are taken together with the nitrogen to form a ring having 5 or 6 atoms, or a ring having 6 atoms and containing oxygen, into enamines represented by the formula

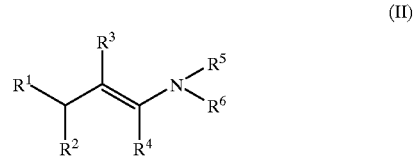

(II)

in which the symbols R$^1$–R$^6$ have the meanings assigned above, or into imines represented by the formula

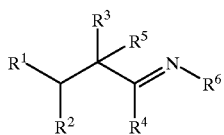

(III)

in which the symbols $R^1$–$R^4$ and $R^6$ have the meanings assigned above and $R^5$ is hydrogen, by means of catalysts of Rh, Ir or Ru having at least one chiral phosphorated ligand, the method being characterised in that the phosphorated ligand in the catalyst of Rh, Ir or Ru is a ligand represented by the formula

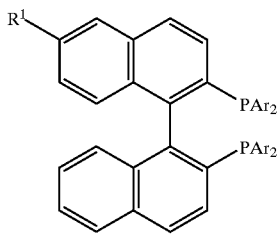

(V)

in which Ar represents a phenyl or tolyl group, $R^1$ is a unit of the type Z—B—, in which B is a group linking the polymer Z with the ligand, selected from among the groups —O—C(O)—(CH$_2$)$_n$—, —NH—C(O)—(CH$_2$)$_n$—, —O—(CH$_2$)$_n$—, —NH—(CH$_2$)$_n$— and —(CH$_2$)$_n$—, n being a whole number from 1 to 10, and Z is a polymer or copolymer selected from among silica, polystyrene, the polyamides, TENTAGEL resins (grafted copolymers having a low crosslinked polystyrene matrix on which polyethyleneglycol or polyoxyethylene is grafted), the functionalised polystyrene of the Merrifield resin type, aminomethylated polystyrene, or [4-(hydroxymethyl)phenoxymethyl] polystyrene ("Wang resin"); or in which the phosphorated ligand is a ligand represented by formula

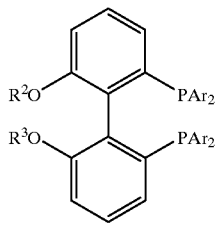

(VI)

in which Ar is a phenyl or tolyl group, $R^2 \neq R^3$ and $R^2$ and $R^3$ represent hydrogen or a unit of the type Z—B'—, B' being a group linking the polymer Z and the ligand, selected from among the groups —C(O)—, —(CH$_2$)$_m$— or —NH—C(O)—(CH$_2$)$_m$—C(O)—, m being a whole number from 1 to 4, and Z being a polymer as defined above, $R^2=R^3=H$ being excluded.

We found that the ligands according to formulae (V) and (VI) are very useful for preparing metallic catalysts which are active in the stereospecific isomerisation of allylamines into amines or chiral imines. More particularly, they proved to be highly effective in the isomerisation of diethyl geranylamine and of diethyl nerylamine. We were able to verify that the immobilisation of the ligands used in the present invention has no negative effect on their performance, and even enables advantageous and unanticipated results to be obtained by comparison with non-immobilised ligands.

The polymers or copolymers which may be used as carriers for the ligands in the context of the present invention are the state-of-art ones and include silica, polyamides and polystyrene, particularly functionalised and, as the case may be, cross-linked polystyrenes. Non-limiting examples of this type of polymer are functionalised polystyrenes cross-linked to divinyl benzenes (called Merrifield resins), TENTAGEL resins (grafted copolymers having a low crosslinked polystyrene matrix on which polyethyleneglycol or polyoxyethylene is grafted), functionalised polystyrene of the Wang resin type, or [4-(hydroxymethyl)phenoxymethyl] polystyrene, and aminomethylated polystyrene.

The preferred ligands of formula (V) are those in which $R^1$ is a unit of the type —(CH$_2$)$_3$—C(O)O—CH$_2$—Z, Z being the resin of the "Wang" type, or a unit of the type —(CH$_2$)$_3$—C(O)NH—CH$_2$—Z, Z being polystyrene.

Regarding formula (VI) ligands, those in which $R^2$ is a unit of the type —(CH$_2$)$_2$—(O—C$_2$H$_4$)$_x$—Z or —C(O)—(CH$_2$)$_2$—C(O)—NH—(CH$_2$)$_2$—(O—C$_2$H$_4$)$_x$—Z are preferred, in which x is a whole number of about 60 and Z is polystyrene. These are then compounds of the formula (VI) in which the active ligand is linked to a resin of the so-called "Tentagel" type, from the oxygen atom.

Formula (VI) ligands, which constitute another object of the present invention, are new chemical compounds. They are synthesised from 6,6'-bis(diphenylphosphino)biphenyl-2,2'-diol (VII) [obtained by cleavage of (6,6'-dimethoxybiphenyl-2,2'-diyl)-bis(diphenyl phosphine), see EP-A-398 132], by reacting with the desired polymer or a derivative thereof, as shown in the following reaction scheme:

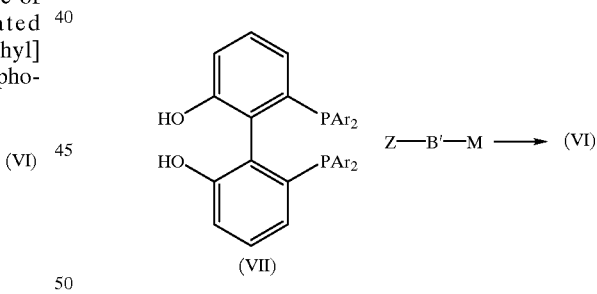

In the above scheme, Ar, Z and B' have the meanings assigned above and M is a suitable leaving group enabling the diol (VII) to be coupled to the polymer used, or to a derivative thereof. Suitable M groups are known to the person skilled in the art, and non-limiting examples may be found below. The choice of M group of course depends on many factors such as, for example, the reactivity of the linking group B', and the person skilled in the art is able to select leaving groups M in accordance with his or her chemical knowledge.

Complexes used as metallic complexes which may serve as a catalyst for the isomerisation reaction are those of Rh, Ir and Ru, preferably Rh complexes.

The principle of synthesis of active complexes of rhodium is known. This synthesis involves reacting chiral phosphines of the above formulae with a suitable precursor complex of Rh(I). As examples of the latter we cite complexes of the type [Rh(ene)$_2$Y]$_2$ or [Rh diene Y]$_2$, which react with the phosphorated ligands in the presence of a silver salt of the formula AgX, or complexes of the type [Rh(diene)$_2$]X, which also react with phosphorated ligands, giving rise to catalytically active complexes according to the invention. If required, synthesis of the active complexes is carried out after treatment with hydrogen, at pressures which may be as high as 100 bars, preferably up to 40 bars. The active complexes themselves may be described by the general formulae [RhL*(ene)$_2$]$^+$X$^-$, [RhL*diene]$^+$X$^-$, [RhL*]$^+$X$^-$ or [RhL*$_2$]$^+$X$^-$. In these formulae, L* indicates a phosphorated chiral ligand as defined by the formulae (V), (IX) or (X) defined above, ene indicates an olefin such as for example ethylene, propylene or butene, diene indicates a diene such as for example 1,3-butadiene, 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclo-octadiene, or norbornadiene. The preferred dienes are 1,5-cyclo-octadiene (hereinafter abbreviated to "COD") and norbornadiene (hereinafter abbreviated to "NBD"). X$^-$ indicates an anion such as a halide, ClO$_4^-$, BF$_4^-$, B(C$_6$H$_5$)$_4^-$, PF$_6^-$, PCl$_6^-$, CH$_3$COO$^-$, CF$_3$COO$^-$, SbF$_6^-$, AsF$_6^-$, CH$_3$SO$_3^-$, FSO$_3^-$ or CF$_3$SO$_3^-$, and Y indicates a bridging anion selected from among the halides.

We found that when CF$_3$SO$_3^-$, common name triflate, was used as a counter-ion in the process of the invention, advantageous results were obtained. Not only did the use of this ion frequently lead to the highest conversions and enantiomeric excesses (ee), by comparison with the ions described and used to date in the type of isomerisation which is the object of the present application; it also allowed a reduction in the proportion of the catalyst relative to the substrates. This effect will be more evident from reading the examples presented below.

The complexes of iridium which can be used in the process of the invention are synthesised in way similar to those of rhodium, from a phosphorated ligand and a suitable precursor complex. As an example of the latter we hereby cite the formulae [Ir(COD)Y]$_2$, IrY$_3$, [IrY$_6$]$^{2-}$ in which COD signifies 1,5-cyclo-octadiene and Y signifies a bridging anion which is a halide. As regards Ru, several known complexes of this metal lend themselves to use in the process of the invention as a precursor complex. By way of a non-limiting example, only the species [Ru$_2$(ACOO)$_4$ (H$_2$O)(diene)$_2$] (A=non-substituted alkyl or aryl group or halogen), [RuY$_2$(aryl)]$_2$ (aryl=aryl group such as benzene, toluene, cymene, Y=bridging anion selected from among the halides).

The person skilled in the art is familiar with a large number of prochiral allylamines that may be used as the substrate in the process of the invention and are designated by the formula (I). We therefore refer here to the examples of suitable allylamines cited in patent EP-B-068 506, page 4, lines 1–7, or the prochiral allylamines respectively. The amines cited in this prior art are hereby included by reference.

The most valued substrates for isomerisation according to the invention are diethyl nerylamine and diethyl geranylamine. As other preferred substrates of the present invention, we cite here cyclohexyl geranylamine, methylcyclohexyl geranylamine and (E)- and (Z)-N,N-diethyl-7-hydroxy-3,7-dimethyl 2-octenylamine [see K. Tani, Pure Appl. Chem. 1985, (57), 1845 and J. Am. Chem. Soc. 1984 (106) 5208]. After hydrolysis of the chiral enamine which forms during the process, the process of the invention yields optically active citronellal.

The process of the invention enables allylamines to be isomerised with conversions which may reach 100% and enantiomeric excesses of more than 80%, often approaching 100%. The result depends on the complex and the phosphine used, and also on the reaction conditions, such as the reaction time, temperature, and the amount of catalyst relative to the substrate, etc. The person skilled in the art is capable of adjusting these parameters so as to optimise the reaction yield.

When the method of the invention is performed, the active complex may be synthesised in advance and then added to the reactor, or it may be produced in situ from the precursor complex, such as one described earlier, and the selected chiral phosphine.

The amount of catalyst relative to the substrate may vary from 0.05 mol % to 20 mol %. The catalyst will preferably be used in a proportion of 0.1 to 5 mol %, relative to the substrate. A particular advantage of the use of immobilised ligands such as those described in the present application resides in the fact that separation of the reaction mixture from the catalyst is particularly easy, as it can be done by simple decantation or filtration without the need for distillation. Following separation from the reaction mixture, the catalyst may be reused in the isomerisation reaction, and only very slight deactivation of the catalyst is observed even after several repetitions of the method with the same catalyst.

If necessary, a suitable quantity of the precursor complex is added after a certain number of repetitions, as release of the metal into the reaction medium is occasionally observed. We obtained the best results by using an alcohol, such as ethanol, an ester, such as ethyl acetate, or tetrahydrofuran (THF) as the solvent. These solvents are preferred according to the invention, the best results having been obtained with THF.

The isomerisation reaction may be performed at a temperature between 0° C. and 150° C., preferably between 40 and 110° C. The temperature may be selected as a function of the substrate and of the solvent used, this being within the means of the person skilled in the art.

The invention will now be described in greater detail in the experimental part which follows.

MODES OF EXECUTION OF THE INVENTION

A. General Preparation of the Starting Compounds

The allylamines of formula (I) are commercially available products. The diethyl geranylamine used had a purity of 94–99% (determined by gas phase chromatography; source : Dérivés Résiniques and Terpéniques, Castets, France), and the diethyl nerylamine used had a purity of 95% and was prepared as described by K. Takabe, Y. Yamada, T. Katagiri, J. Tanaka in Org. Synth. 1988, (67), 48.

The phosphorated ligands of formula (V) were obtained from Oxford Asymmetry Ltd, Milton Park, Great Britain. The 6,6'-(dimethoxybiphenyl-2,2'-diyl)-bis(diphenyl phosphine) was supplied by Hoffmann-La Roche AG, Basle, Switzerland.

The precursor complexes for producing the active complexes of the invention may be synthesised in a way known to the person skilled in the art, or as described in the reference documents EP-A-398 132, EP-A-643 065 or WO 95/21176.

B. Preparation of Ligands of Formula (VII)

a) (−)-(S)-6,6'-Bis(diphenylphosphino)biphenyl-2,2'-diol

To a solution of 6,6'-(dimethoxybiphenyl-2,2'-diyl)-bis (diphenylphosphine) ([α]$^{20}_D$=−42.5°, c=1.0, CHCl$_3$, 300 mg, 0.515 mmol) in 3 ml CH$_2$Cl$_2$, 120 µl (1.24 mmol) BBr$_3$ was added dropwise at 0°. After 18 h at 20°, the solution was cooled again to 0° before a slow hydrolysis. The mixture was diluted with $CH_2Cl_2$, washed with water and $NaHCO_3$, dried and concentrated under vacuum, to obtain the desired quantity of the product.

Melting point: 217° C.
$[\alpha]^{20}_{365} = -109°$ (c=0.8, $CHCl_3$)
IR: 3533, 3051, 2922, 1567, 1446, 1433, 1279, 1205
$^1$H-NMR: 1.6(broad, 2H); 6.8(m, 4H); 7.15(m, 4H); 7.25 (m, 18H) δ ppm
$^{13}$C-NMR: 116.4(2d); 126.9(2d); 128.1(2d); 128.2(4d); 128.5(4d); 128.6(4d); 129.1(2d); 130.6(2d); 133.1(2d); 134.5(2d); 136.7(2s); 137.2(2s); 141.2(4s); 154.3(2s) δ ppm
$^{31}$P-NMR: −16.20 at −40°; MS: 554($M^+$,5): 491(13), 369(100), 262(50), 183(65).

b) (−)-(S)-6,6'-Bis(diphenylphosphino)biphenyl-2,2'-diol Fixed on to Tentagel of Approximate Formula

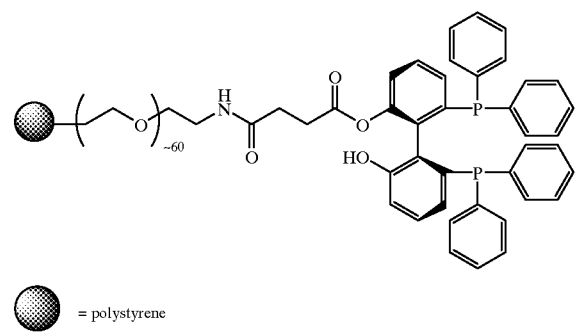

= polystyrene 100 mg (0.18 mmol) of the starting diol was added to a suspension of N,N-dicyclohexylcarbodiimide (40.3 mg, 0.195 mmol), 4-dimethylaminopyridine (1.8 mg, 0.015 mmol) and 761 mg (0.19 mmol) O-(2-succinylaminoethyl)polyethylene glycol fixed on to polystyrene (Fluka, #86358) in 5 ml of $CH_2Cl_2$. The suspension was stirred for 24 h at 20°, prior to filtration and washing with a saturated solution of $NaHCO_3$, water, 1:1 $THF/H_2O$, THF, ethanol, $CH_2Cl_2$ and diethyl ether. After drying at 50° for several hours, 664 mg (77%) of the immobilised ligand was obtained.

IR (KBr): 3600, 3000, 2800, 1800, 1600 $cm^{-1}$
$^{31}$P-NMR: −15.27; −15.40 δ ppm c) (−)-(S)-6,6'-Bis(diphenylphosphino)biphenyl-2,2'-diol Fixed on to Tentagel of Approximate Formula

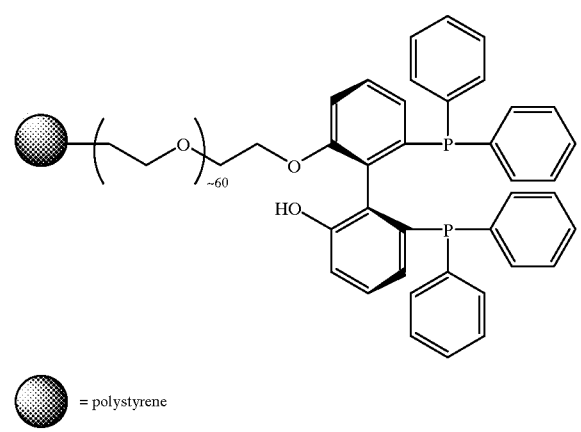

= polystyrene

117 μl of a 1.6 M solution of n-butyl lithium in hexane was added dropwise to a solution of the starting diol (100 mg, 0.18 mmol) in 2 ml THF. After 1 h, this solution was added to a suspension of O-(2-bromoethyl)polyethylene glycol fixed on to polystyrene (Fluka, #86357, 487 mg, 0.18 mmol) in 5 ml THF. The suspension was stirred for 48 h, then filtered and washed successively with water, 1:1 THF/$H_2O$, THF, diethyl ether, $CH_2Cl_2$ and diethyl ether, before drying for 18 h at 50° under high vacuum. 412 mg (72%) of the desired immobilised ligand was thus obtained.

IR (KBr): 3600, 3000, 2900, 2000, 1800, 1600, 1500 $cm^{-1}$ $^{31}$P-NMR: −14.73

C. General Procedure of the Process for Isomerisation of Diethyl Geranylamine and Diethyl Nerylamine In a glove box, 3.325 ml of a 0.01 M solution of the precursor complex, for example [Rh(COD)$_2$]$^+$SO$_3$CF$_3^-$, in THF were added to 0.03325 mmol of the respective ligand in THF (6.2 ml), in a 100-ml flask equipped with a tap. The solution was stirred for 1 h, then 2.615 g (12.5 mmol) diethyl geranylamine or diethyl nerylamine was added. The flask was fitted with a condenser connected to a Schlenk line, purged with argon and brought to reflux. A constant temperature was maintained during the reaction time indicated in the table below. The solution was then cooled to 0° C. before separating the solution from the solid catalyst by decantation. The catalyst can then be reused in the same reaction by simply adding a fresh quantity of the substrate. The process of isomerisation may then be repeated several times, up to about 36 times. To obtain the desired product in the pure state, the mixture or mixtures obtained were hydrolysed by adding 5 ml of a 1:4 mixture of acetic acid and water, and extracted with diethyl ether. The extract was washed with water (10 ml), 15% NaOH (2×10 ml) then to neutrality with water, and then dried over $MgSO_4$. After concentrating the resulting solution, the residue was distilled in a bulb-to-bulb oven or, if necessary, over residues, to yield optically active citronellal, with a conversion and an enantiomeric excess such as that indicated in the tables below.

D. Examples of the Use of Specific Ligands in the Isomerisation of Diethyl Geranylamine and of Diethyl Nerylamine

GENERAL COMMENT

In the tables below, the conversions and the enantiomeric excesses (ee) always refer to the citronellal obtained after the isomerisation reaction and hydrolysis of the enamine thus obtained. Isolation of the enamine and its hydrolysis are performed by methods familiar to the person skilled in the art, which are, for example, described in patent EP-B-068 506 cited above. (±) indicates whether the preponderant quantity of citronellal was present in the form of the (+) or of the (−) isomer. The enantiomeric excesses were determined by chromatography in the gaseous phase on a Brechbuehler SA type column, #27425-025 25 m in length and 0.25 mm in diameter. Unless otherwise indicated under "mode of execution", the precursor complex and the ligand were always used in a concentration of 0.25 mol % relative to the substrate.

EXAMPLE 1

The ligand used was (R)-BINAP grafted on to a Wang-type resin of formula

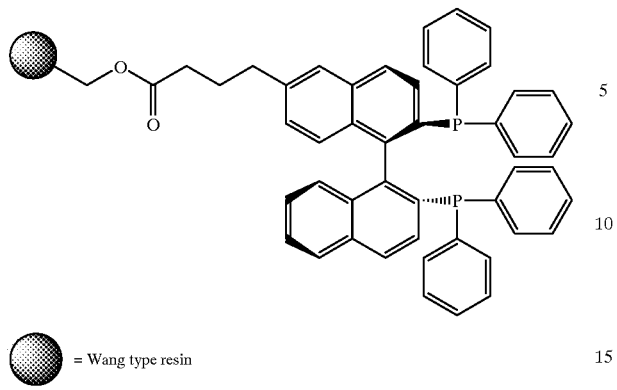

● = Wang type resin

The following results were obtained:

| Precursor complex | Catalyst/ substrate ratio | Substrate | Reaction time | Temp./ ° C. | Conversion | ee | (+/−) | Solvent |
|---|---|---|---|---|---|---|---|---|
| [(COD)₂Rh]SO₃CF₃ | 0.25% | DEGA | 20 h | 66 | 100% | 98% | − | THF |
| [(COD)₂Rh]SO₃CF₃ | 0.25% | DENA | 20 h | 66 | 100% | 98% | + | THF |

DEGA = diethyl geranylamine
DENA = diethyl nerylamine

In this mode of execution, the immobilised catalyst may be separated from the reaction medium by simple decantation. By adding 0.25 mol % of the precursor complex after each isomerisation test, the reaction could be repeated 36 times.

The following results were obtained:

| Precursor complex | Catalyst/ substrate ratio | Substrate | Reaction time | Temp./ ° C. | Conversion | ee | (+/−) | Solvent |
|---|---|---|---|---|---|---|---|---|
| [(COD)₂Rh]SO₃CF₃ | 0.25% | DEGA | 20 h | 66 | 79% | 88% | + | THF |

DEGA = diethyl geranylamine

EXAMPLE 2

The following ligand was used:

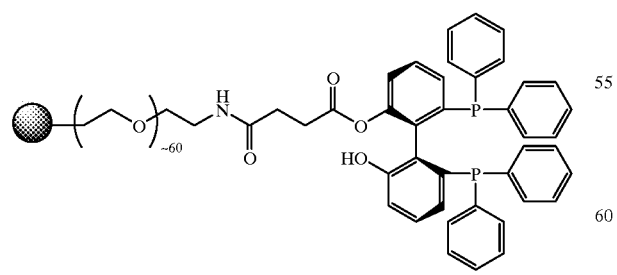

● = polystyrene

EXAMPLE 3

The following ligand was used:

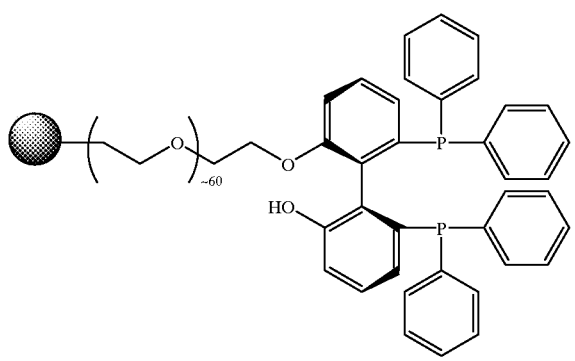

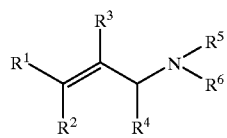
= polystyrene

The following results were obtained:

| Precursor complex | Catalyst/ substrate ratio | Substrate | Reaction time | Temp./ ° C. | Conversion | ee | (+/−) | Solvent |
|---|---|---|---|---|---|---|---|---|
| [(COD)$_2$Rh]SO$_3$CF$_3$ | 0.25% | DEGA | 20 h | 66 | 48% | 96% | + | THF |

DEGA = diethyl geranylamine

What is claimed is:

1. A process for stereospecific isomerisation of prochiral allyl systems represented by the formula

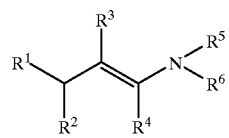
(I)

in which $R^1 \neq R^2$ and each represents an alkyl or alkenyl group, containing 1 to 12 carbon atoms, or an aryl group, optionally substituted by a hydroxy group, $R^3$ and $R^4$ represent independently from one another hydrogen, a $C_1$ to $C_{12}$ alkyl or alkenyl group, or an aryl group, $R^5$ is hydrogen or an alkyl or cycloalkyl group, containing 1 to 8 carbon atoms, $R^6$ is an alkyl or cycloalkyl group, containing 1 to 8 carbon atoms, or $R^5$ and $R^6$ are taken together with nitrogen to form a ring having 6 atoms and containing oxygen, into enamines represented by the formula

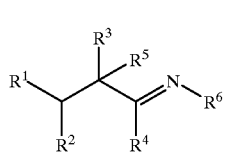
(II)

in which the symbols $R^1$ to $R^6$ have the meanings assigned above, or into imines represented by the formula

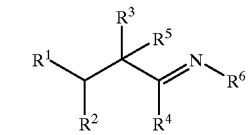
(III)

in which the symbols $R^1$ to $R^4$ and $R^6$ have the meanings assigned above and $R^5$ is hydrogen, with the aid of catalysts of Rh, Ir or Ru having at least one chiral phosphine ligand, and in the presence of a solvent, the process being characterised in that the phosphine ligand is a ligand represented by the formula

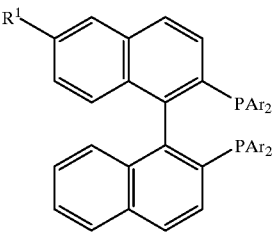
(V)

in which Ar represents a phenyl or tolyl group, $R^1$ is a unit of the type Z—B—, in which B is a group linking the polymer Z with the ligand, selected from among the groups —O—C(O)—(CH$_2$)$_n$, —NH—C(O)—(CH$_2$)$_n$—, O—(CH$_2$)$_n$—, —NH—(CH$_2$)$_n$— and (CH$_2$)$_n$—, n being a whole number from 1 to 10, and Z is a polymer or copolymer selected from among silica, polystyrene, polyamides, grafted copolymers having a low crosslinked polystyrene matrix on which polyethyleneglycol or polyoxyethylene is grafted, functionalised polystyrene of the Merrifield resin type, aminomethylated polystyrene, or (4-hydroxymethyl) phenoxymethyl) polystyrene; or in which the phosphine ligand is a ligand represented by formula

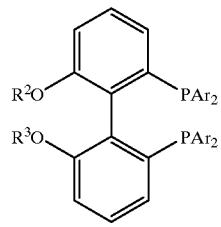

(VI)

in which Ar is a phenyl or tolyl group, $R^2$ and $R^3$ represent hydrogen or a unit of the type Z—B'—, B' being a group linking the polymer Z and the ligand, selected from among the groups —C(O)—, —$(CH_2)_m$— or —NH—C(O)—$(CH_2)_m$—C(O)—, m being a whole number from 1 to 4, and Z being a polymer as defined above, $R^2=R^3=H$ being excluded.

2. The process according to claim 1, characterised in that the ligand used is a ligand of formula (V) in which in which $R^1$ is a unit of the type —$(CH_2)_3$—C(O)O—$CH_2$—Z, Z being a resin of the Wang type, or a unit of the type —$(CH_2)_3$—C(O)NH—$CH_2$—Z, Z being polystyrene.

3. The process according to claim 1, characterised in that the ligand used is a ligand of formula (VI) in which $R^3$ is hydrogen and $R^2$ is a unit of the type —$(CH_2)_2$—(O—$C_2H_4$)$_x$—Z or —C(O)—$(CH_2)_2$—C(O)—NH—$(CH_2)_2$—(O—$C_2H_4$)$_x$—Z, in which x is a whole number of about 60 and Z is polystyrene.

4. The process according to claim 1, characterized in that the catalyst used an active complex of Rh, of formula $[RhL^*(ene)_2]^+X^-$, $[RhL^*diene]^+X^-$, $[RhL^*]^+X^-$ or $[RhL^*_2]^+X^-$, in which L* represents a phosphine chiral ligand as defined in claim 1, "ene" represents an olefin, "diene" represents a diene, and $X^-$ stands for a mono anion.

5. The process according to claim 4, wherein the olefin comprises at least one of ethylene, propylene, or butene, the diene comprises at least one of 1,3-butadiene, 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene, or norbornadiene, and the mono anion comprises at least one of $ClO_4^-$, $BF_4^-$, $B(C_6H_5)_4^-$, $PF_6^-$, $PCl_6^-$, $CH_3COO^-$, $CF_3COO^-$, $SbF_6^-$, $AsF_6^-$, $CH_3SO_3^-$, $FSO_3^-$ or $CF_3SO_3^-$.

6. The process according to claim 4, characterised in that the diene is norbornadiene or 1,5-cyclo-octadiene.

7. The process according to claim 5, characterised in that the anion X is $CF_3SO_3^-$.

8. The process according to claim 1, characterised in that the allyl amine is geranyl diethylamine, neryl diethylamine, cyclohexyl geranylamine, methylcyclohexyl geranylamine, or (E)- or (Z)-N,N-diethyl-7-hydroxy-3,7-dimethyl 2-octenylamine.

9. The process according to claim 1, characterised in that the catalyst of Rh, Ir or Ru is used in a concentration of between 0.05 mol % and 20 mol % relative to the substrate.

10. The process according to claim 9, characterised in that the said catalyst is used in a concentration of between 0.1 and 5 mol % relative to the substrate.

11. The process according to claim 1, characterised in that the reaction is carried out at a temperature of between 0° C. and 150° C.

12. The process according to claim 11, characterised in that the reaction is carried out at temperatures of between 40 and 110° C.

13. The process according to claim 1, characterised in that the solvent used is tetrahydrofuran.

14. An immobilised ligand of formula

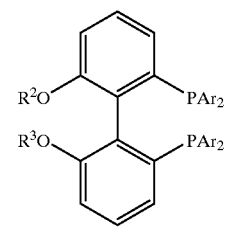

(VI)

in which Ar is a phenyl or tolyl group, $R^2$ and $R^3$ represent hydrogen or a unit of the type Z—B'—, B' being a group linking the polymer Z and the ligand, selected from among the groups —C(O)—, —$(CH_2)_m$— or —NH—C(O)—$(CH_2)_m$—C(O)—, m being a whole number from 1 to 4, and Z is a polymer or copolymer selected from among silica, polystyrene, polymides, grafted polymers having a low cross linked polystyrene matrix on which polyethyleneglycol or polyoxyethylene is grafted, functionalised polystyrene of the Merrifield resin type, aminomethyl polystyrene or, (4-(hydroxymethyl)phenoxymethyl) polystyrene, $R^2=R^3=H$ being excluded.

15. The ligand according to claim 14, characterised in that $R^2$ is a unit of the type —$(CH_2)_2$—(O—$C_2H_4$)$_x$—Z or —C(O)—$(CH_2)_2$—C(O)—NH—$(CH_2)_2$—(O—$C_2H_4$)$_x$—Z, in which x is a whole number of about 60 and Z is polystyrene.

* * * * *